United States Patent [19]

Bennett

[11] Patent Number: Plant 5,260

[45] Date of Patent: Jul. 17, 1984

[54] MINIATURE ROSE PLANT

[76] Inventor: Cecilia L. D. Bennett, 489 Minot Ave., Chula Vista, Calif. 92010

[21] Appl. No.: 463,535

[22] Filed: Feb. 3, 1983

[51] Int. Cl.[3] ..... A01H 5/00

[52] U.S. Cl. ..... Plt./8

[58] Field of Search ..... Plt./8

*Primary Examiner*—Robert E. Bagwill

[57] ABSTRACT

The subject of the present disclosure is a new and distinct variety of miniature rose plant characterized by its urn shaped exhibition form and the creamy lemon color of the bloom.

1 Drawing Figure

1

The present invention relates to a new and distinct variety of hardy, dwarf, miniature bush plant of the miniature class; the variety being primarily characterized as a medium yellow.

The variety is further characterized by:

The unique urn shape of the bloom as the flower opens.

The abundance of medium green foliage in the plant.

The fast repeat of blooms.

A slight tea fragrance.

The plant ranges in height from 12 to 18 inches. The branches short, slender but wirey. Blooms are held erect. Grows equally well in hothouse or outdoors.

The present variety of miniature rose was originated by me at Tiny Petal's Nursery, located at Chula Vista, Calif., under careful observation, and is a cross of "Sunbonnet" a floribunda introduced in 1967 by (Weeks and Swim) U.S. Plant Pat. No. 2,818, the seed parent, and "Rise 'n Shine" introduced by Sequoia Nursery, in 1977. U.S. Plant Pat. No. 4,231, as the pollen parent.

Subsequent to origination of the variety I successfully reproduced it by cuttings and budding at Tiny Petal's Nursery located at aforesaid locale with reproductions coming true in all respects.

The color photographs illustrate the variety.

Referring now specifically to the new and distinct variety of miniature rose plant, the following is a detailed description thereof in outline; all major color plate identification being by reference to the British Colour Council Horticultural Chart.

Type: Hardy, dwarf, compact, seedling, greenhouse, outdoors, cut flowers, garden decoration and potted plant.

Class: Miniature.

Variety name: "Fairest of Fair".

Flowers borne: One to a stem.

Quantity of bloom: Very prolific both in hothouse and the outdoors.

Bud:

*Peduncle.*—Short, slender, erect, reddish, ½ to 1 inch in length.

*Hairs.*—Very minute, reddish.

*Before calyx breaks.*—Size small. Form; ovoid, sepals extend well out past the end of the bud and flare outward. Color medium green.

*As calyx opens.*—Color creamy yellow. Opens well in all weather.

Bloom:

*Size when fully open.*—1 to 1½ inches in diameter.

2

*Petalage.*—Double averaging from 20 to 25 petals arranged regularly.

*Form.*—Center petals slightly smaller than outer petals. Opens slowly with a gentle reflexing of the petals. Open flower reveals a generous amount of stamens surrounding a green pistil.

Petals: Good substance, matt surface topside and underside of the petals.

*Shape.*—Outside petals, broad lanceolate with broad tip. Intermediate petals, broad lanceolate with broad tip. Inside petals, slightly elongated with broad tip.

Color: Newly opened flowers as grown by me at Chula Vista, Calif.

*Outer petal.*—Topside surface mimosa yellow 602/1, page 143, with outer edge of petals a softer shade of mimosa yellow, 602/3, page 143.

*Outer petal.*—Topside surface mimosa yellow 602/1, page 143, with a soft blending of mimosa yellow 602/3, at the top of the petal.

*Outer petal.*—Underside surface mimosa yellow 602/1, page 143, with a soft blending of mimosa yellow 602/3, page 143, at the top of the petal.

*Intermediate petal.*—Topside surface mimosa yellow 602/1, page 143, with a soft blending of mimosa yellow 602/3, page 143, at the top of the petal.

*Intermediate petal.*—Underside surface mimosa yellow 602/1, page 143, with a soft blending of mimosa yellow 602/3, page 143, at the top of the petal.

*Inner petal.*—Topside surface mimosa yellow 602/1, page 143, with a soft blending of mimosa yellow 602/2, page 143, at the top of the petal.

*Inner petal.*—Underside surface mimosa yellow 602/1, page 143, with a soft blending of mimosa yellow 602/2, page 143, at the top of the petal.

Behavior: Opens well in all weather. Opens slowly. Turns paler 3 to 4 days after fully blooming. Excellent volunteer repeat blooming.

Reproductive organs:

*Stamens.*—Abundant, arranged evenly around the pistil.

*Filament.*—Varying lengths.

*Pollen.*—Abundant.

*Pistil.*—Short and green in color.

*Styles.*—Short, irregular.

*Ovaries.*—All encased in calyx.

*Hips.*—None.

Foliage:

*Leaves.*—Compact of five to seven, small, glossy, have a tendancy to arch downward.

*Leaflets.*—Shape, narrow, arrow shaped with red edging.

*Margin.*—Very serrated.

*Color.*—Medium green.

Rachis: Medium length, underside thorny.

*Stipule.*—Medium length, medium width.

Growth:

*Habit.*—Dwarf, much branched, heavily foliaged.

*Growth.*—Vigorous.

*Canes.*—Short, slender, strong, thorny.

*Main stem.*—Color greyish green.

*Thorns.*—Small, fine, reddish on young growth, very light grey on older branches.

*Prickles.*—A few.

*Branches.*—Color: medium green, reddish on new growth.

The miniature rose plant and its flowers as herein described may vary in slight detail due to climatic, soil and cultural conditions under which the variety may be grown; the present description being of the variety as grown by me at Chula Vista, Calif.

I claim:

1. A new and distinct variety of miniature rose plant of hardy, dwarf, bushy, much branched habit, substantially as illustrated and described, characterized by buds and flowers of creamy yellow.

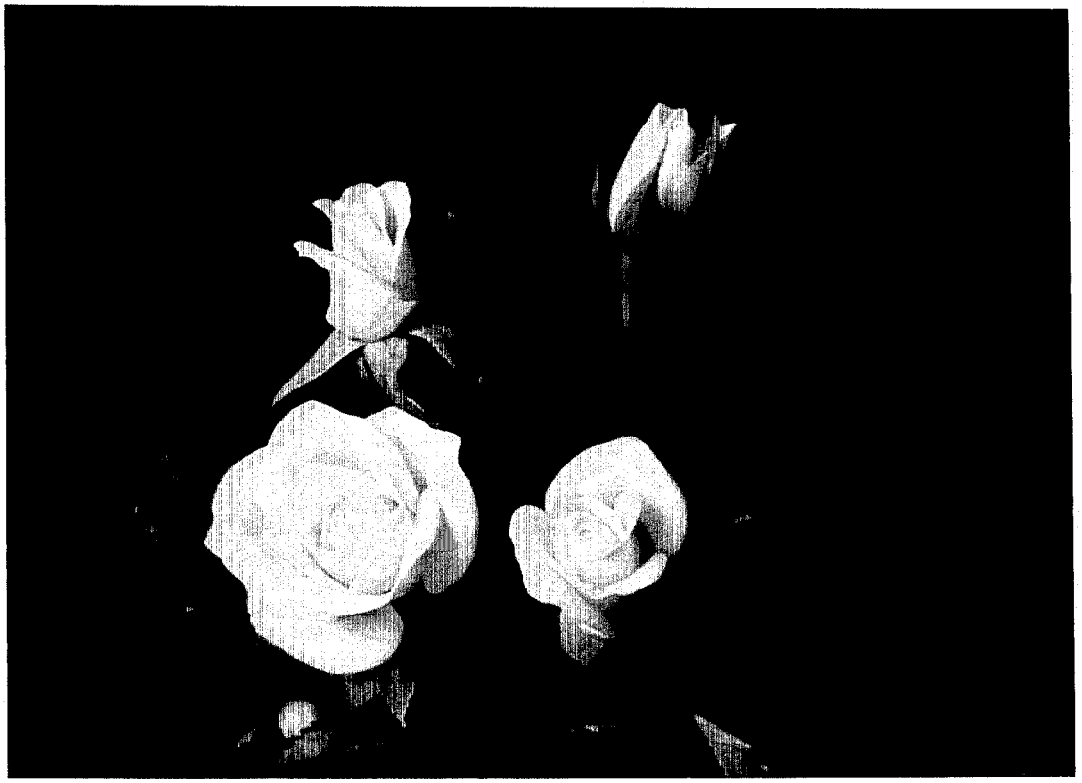

* * * * *